United States Patent
Frye et al.

(10) Patent No.: US 9,802,834 B2
(45) Date of Patent: Oct. 31, 2017

(54) PRODUCTION OF NANOCRYSTALLINE METAL POWDERS VIA COMBUSTION REACTION SYNTHESIS

(75) Inventors: John G. Frye, Richland, WA (US); Kenneth Scott Weil, Richland, WA (US); Curt A. Lavender, Richland, WA (US); Jin Yong Kim, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 1001 days.

(21) Appl. No.: 12/700,923

(22) Filed: Feb. 5, 2010

(65) Prior Publication Data

US 2011/0194970 A1 Aug. 11, 2011

(51) Int. Cl.
| | |
|---|---|
| *B22F 9/24* | (2006.01) |
| *C01G 41/00* | (2006.01) |
| *C01G 39/02* | (2006.01) |
| *B22F 1/00* | (2006.01) |
| *C01G 33/00* | (2006.01) |
| *C01G 41/02* | (2006.01) |
| *C01G 47/00* | (2006.01) |
| *C22C 1/04* | (2006.01) |

(Continued)

(52) U.S. Cl.
CPC ............ *C01G 39/02* (2013.01); *B22F 1/0044* (2013.01); *B22F 9/24* (2013.01); *C01G 33/00* (2013.01); *C01G 41/02* (2013.01); *C01G 47/00* (2013.01); *C22C 1/045* (2013.01); *C22C 1/058* (2013.01); *C22C 27/04* (2013.01)

(58) Field of Classification Search
CPC .............................. C22C 2200/04; C01G 1/02
USPC .................. 75/343, 351, 363–374, 392, 414, 75/611–623; 148/422, 423; 420/425, 420/426, 429–433; 977/773–777, 810; 423/1, 49–68, 592.1, 593.1, 594.8, 423/594.13, 605–607, 594.17
IPC ........... C01B 13/00,13/14; C01G 47/00, 41/02, 39/02, 33/00

See application file for complete search history.

(56) References Cited

U.S. PATENT DOCUMENTS

| | | |
|---|---|---|
| 3,330,697 A | 7/1967 | Pechini |
| 5,061,682 A | 10/1991 | Aksay et al. |

(Continued)

OTHER PUBLICATIONS

Sergio L. Gonzales-Cortes, Serbia M. A. Rodulfo-Baechler, Tiancun Xiao, and Malcom L. H. Green, "Rationalizing the catalytic performance of γ-alumina-supported Co(Ni)—Mo(W) HDS catalysts prepared by urea-matrix combustion synthesis," Catalysis Letters, vol. 111, Nos. 1-2, pp. 57-66, Oct. 2006.*

(Continued)

*Primary Examiner* — Scott Kastler
*Assistant Examiner* — Vanessa Luk
(74) *Attorney, Agent, or Firm* — Wells St. John P.S.

(57) ABSTRACT

Nanocrystalline metal powders comprising tungsten, molybdenum, rhenium and/or niobium can be synthesized using a combustion reaction. Methods for synthesizing the nanocrystalline metal powders are characterized by forming a combustion synthesis solution by dissolving in water an oxidizer, a fuel, and a base-soluble, ammonium precursor of tungsten, molybdenum, rhenium, or niobium in amounts that yield a stoichiometric burn when combusted. The combustion synthesis solution is then heated to a temperature sufficient to substantially remove water and to initiate a self-sustaining combustion reaction. The resulting powder can be subsequently reduced to metal form by heating in a reducing gas environment.

14 Claims, 1 Drawing Sheet

(51) Int. Cl.
*C22C 1/05* (2006.01)
*C22C 27/04* (2006.01)

(56) References Cited

U.S. PATENT DOCUMENTS

| | | | |
|---|---|---|---|
| 5,114,702 A | 5/1992 | Pederson et al. | |
| 5,468,427 A * | 11/1995 | Stangle | B82Y 30/00 264/3.4 |
| 5,984,997 A * | 11/1999 | Bickmore et al. | 75/343 |
| 6,171,571 B1 * | 1/2001 | Bedard et al. | 423/594.7 |
| 6,183,716 B1 * | 2/2001 | Sleight et al. | 423/594.13 |
| 6,835,367 B2 * | 12/2004 | James et al. | 423/593.1 |
| 7,022,155 B2 * | 4/2006 | Deegan et al. | 75/336 |
| 7,032,800 B2 | 4/2006 | Subramanian et al. | |
| 7,337,940 B2 | 3/2008 | Subramanian et al. | |
| 7,449,128 B2 * | 11/2008 | Krishna et al. | 252/301.4 R |
| 8,361,178 B2 | 1/2013 | Liu et al. | |
| 2005/0025700 A1 * | 2/2005 | Bulian | B82Y 30/00 423/606 |
| 2005/0129565 A1 | 6/2005 | Ohriner et al. | |
| 2005/0211018 A1 * | 9/2005 | Jurewicz et al. | 75/346 |
| 2008/0223175 A1 * | 9/2008 | Lunk et al. | 75/369 |
| 2010/0136369 A1 | 6/2010 | Ayer et al. | |
| 2010/0279146 A1 | 11/2010 | Rowe et al. | |
| 2011/0194970 A1 | 8/2011 | Frye et al. | |

OTHER PUBLICATIONS

A. S. Mukasyan and P. Dinka, "Novel Approached to Solution-Combustion Synthesis of Nanomaterials," International Journal of Self-Propagating High-Temperature Synthesis, vol. 16, No. 1, pp. 23-35, 2007.*

S. Susikumar and R. Vijayaraghavan, "Solution combustion synthesis of bioceramic calcium phosphates by single and mixed fuels—A comparative study,"Ceramics International, 34, pp. 1373-1379, available online Apr. 10, 2007.*

Mukasyan et al., "Solution combustion synthesis of nanomaterials," Proceedings of the Combustion Institute, 31 (2007), pp. 1789-1795.*

Naik, Mallari A.; Mishra, Braja Gopal; Dubey, Amit, "Combustion synthesized WO3—ZrO2 nanocomposites as catalyst for the solvent-free synthesis of coumarins," Colloids and Surfaces A: Physiochem. Eng. Aspects, 317 (2008), pp. 234-238.*

* cited by examiner

PRODUCTION OF NANOCRYSTALLINE METAL POWDERS VIA COMBUSTION REACTION SYNTHESIS

STATEMENT REGARDING FEDERALLY SPONSORED RESEARCH OR DEVELOPMENT

This invention was made with Government support under Contract DE-AC0576RL01830 awarded by the U.S. Department of Energy. The Government has certain rights in the invention.

BACKGROUND

Tungsten, molybdenum, rhenium, and niobium, as well as alloys based on each, can exhibit the mechanical properties desired for applications requiring high hardness, optimized compressive strength, and good ductility. Exemplary applications can include, but are not limited to, incandescent light filaments, welding tips, and friction stir welding tools. However, synthesis of powders of these materials exhibiting the appropriate composition and microstructure, is relatively costly and difficult to scale-up. In particular, powders having nano-sized crystallites can be especially challenging to produce on a large scale. Accordingly, a need exists for methods of synthesizing nanocrystalline metal powders of tungsten, molybdenum, rhenium, niobium, or their alloys and for nanocrystalline metal powders having the appropriate mechanical properties.

SUMMARY

The present invention encompasses a combustion reaction process for synthesizing a nanocrystalline oxide precursor powder that, upon chemical reduction, forms a nanocrystalline metal powder comprising tungsten, molybdenum, rhenium, and/or niobium. The nanocrystalline metal powder can be subsequently consolidated to form a nanograin metal body via known powder metallurgy processing techniques including uniaxial or cold isostatic pressing, sintering, hot pressing, and hot isostatic pressing. The invention further encompasses the metal powders for use in incadescent light filaments, welding tips, and friction stir welding tools, as well as other applications requiring similar mechanical properties.

As used herein, nanograin can refer to crystallographically distinguishable regions, which typically comprise regular arrays of atoms separated by boundaries of less crystalline order, within a porous or non-porous polycrystalline body or a powder particle on the order of 500 nm or smaller in size. Typically the term "nanograin" is used to describe the microstructure of a final densified body made from nanocrystalline metal powders via a powder metallurgy process (e.g. powder pressing and sintering). "Nanocrystalline" can refer to the microstructure of a porous or non-porous polycrystalline body or powder particle that comprises an aggregate of nanograins (i.e., crystallographically distinguishable regions that are on the order of 500 nm or smaller in size). As used herein, the term "nanocrystalline" is typically reserved to describe the microstructures of the powder particles that are fabricated at various stages of the present invention. For example, while an individual powder particle may be one micron in size, it may be an aggregate of crystallites that are less than 100 nm in size. Accordingly, a particle, as used herein, can refer to the individual pieces or granules that make up a powder mass. As discussed above, each powder particle may in turn be composed of a group of crystallites that are physically or chemically bound together. Alternatively an individual powder particle may be composed of a single crystallite (i.e. a single crystal or single crystallographically distinguishable regular array of atoms).

Methods for synthesizing the nanocrystalline metal powders by a combustion reaction are characterized by forming a combustion synthesis solution by dissolving in water an oxidizer, a fuel, and a base-soluble, ammonium precursor of tungsten molybdenum, rhenium, or niobium in amounts that yield a soichiometric burn when combusted. The combustion synthesis solution is then heated to a temperature sufficient to substantially remove water and to initiate a self-sustaining combustion reaction. Exemplary base-soluble ammonium precursors of tungsten, molybdenum, rhenium, and niobium include, but are not limited to, ammonium metatungstate, ammonium heptamolybdate, ammonium niobate(v) oxalate hydrate, and ammonium perrhenate, respectively.

In some embodiments, alloys of tungsten, molybdenum, rhenium, and/or niobium can be prepared by dissolving a plurality of base-soluble, ammonium precursors in the combustion synthesis solution. Alternatively, or in addition, a nitrate precursor of an alloying metal can be dissolved in the combustion synthesis solution. Exemplary alloying metals can include, but are not limited to, transition metals that form alloy systems readily reduced from their oxides in hydrogen, such as copper, nickel, iron, cobalt, and manganese.

Exemplary oxidizers include, but are not limited to, nitric acid, metal salts (such as nitrates and sulfates), and ammonium nitrate. In some instances, the nitrate precursor can serve as an oxidizer, minimizing, or eliminating the need for addition of a separate oxidizer. The fuel comprises a reducing agent, including but not limited to sugars, amines, keggin-structured metal salts, glycine, and/or a complexing agent.

Products of the combustion reaction comprise tungsten oxide, molybdenum oxide, rhenium oxide, or niobium oxide and are characterized by powder particles having crystallites averaging less than 60 nm in size. In preferred embodiments, the nanocrystallites are less than 60 nm in size.

In another embodiment, a product of the combustion reaction is heated for less than six hours in a reducing atmosphere at a temperature less than 850° C. Reduction of the combustion reaction product can result in a non-oxidized powder. Exemplary reducing atmospheres based on hydrogen can include as much as 100% $H_2$ to as little as 2.75% $H_2$ mixed with an inert gas (e.g., nitrogen, argon, helium, etc.). Alternative reducing atmospheres can be utilized while still falling within the scope and spirit of the present invention.

After reduction, the nanocrystalline metal powder can comprise elemental or alloyed tungsten, molybdenum, rhenium or niobium and is characterized by flowable agglomerated particles consisting of crystallites averaging less than 200 nm in size. Typically, the crystallites average 30-60 nm in size. In preferred embodiments, the crystallites are less than 60 nm in size.

In another embodiment, after reduction, the surfaces of the nanocrystalline metal powder particles can be passivated with a very thin oxide layer. Passivation can occur by cooling the powder to a temperature below 100° C. and then introducing a mildly oxidizing gas. Exemplary gases can include, but are not limited to, carbon dioxide, oxygen diluted in an inert gas, water vapor, or combinations thereof.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions, the various embodiments, including the preferred embodiments, have been shown and described. Included herein is a description of the best mode contemplated for carrying out the invention. As will be realized, the invention is capable of modification in various respects without departing from the invention. Accordingly, the drawings and description of the preferred embodiments set forth hereafter are to be regarded as illustrative in nature, and not as restrictive.

DESCRIPTION OF DRAWINGS

Embodiments of the invention are described below with reference to the following accompanying drawings.

DETAILED DESCRIPTION

Figure 1:
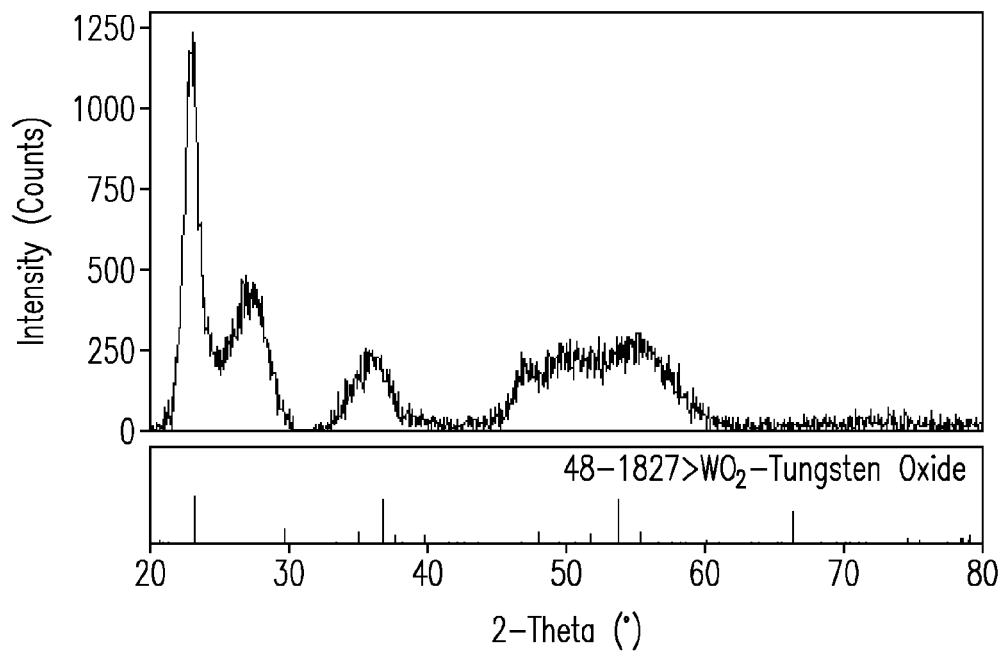
FIG. 1 is an X-ray diffraction pattern for a tungsten oxide powder, which was formed according to embodiments of the present invention, prior to reduction.

The following description includes the preferred best mode of one embodiment of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Embodiments of the present invention involve both the formation of an aqueous solution containing the appropriate precursors as well as the heating of the combustion synthesis solution to dryness and eventual autoignition. Once the precursor is ignited, a self-sustaining combustion reaction produces a final powder comprising an oxide comprising tungsten, molybdenum, rhenium, and/or niobium. According to the present invention, the resulting powder can exhibit a nanocrystalline nature and a high degree of phase homogeneity.

Example: Nanocrystalline Tungsten Powder Synthesis

In the instant example, a tungsten oxide powder, which can be reduced to yield a nanocrystalline tungsten powder, is synthesized. For 100 g of tungsten metal powder, 138.2 g of Ammonium Metatungstate (AMT; $(NH_4)_6H_2W_{12}O_{40} \cdot 5H_2O$, F.W.=3048.1 g/mole, % W by weight=72.3%) is required as a tungsten source. Additional combustion synthesis solution materials include nitric acid and glycine. In order to produce the necessary stoichiometric burn when combusted, equal amounts of oxidizing and reducing capacity must be present in the combustion synthesis solution. Additional details regarding the determination of oxidizing and reducing capacities of various materials is provided by J. J. Kingsley and L. R. Pedersen in "Energetic Materials in Ceramic Synthesis" (Mat. Res. Soc. Symp. Proc. 296 (1993) 361-366), which details are incorporated herein by reference. Briefly, the molecular formulas of each of the reagents are determined to be either net oxidizing agents or net reducing agents on a per mole basis. The relative molar ratios of the reagents required for a stoichiometric burn can then be calculated. The oxidizing and reducing capacities for the reagents of the present example are determined as follows.

For $AMT = (NH_4)_6H_2W_{12}O_{40}$ $$N = 6 \cdot 0 = 0$$
$$H = 26 \cdot -1 = -26$$
$$O = 40 \cdot +2 = +80$$
$$W = 12 \cdot -6 = -72$$
$$\overline{\text{Sum} = -18 \text{ per mole (net reducing)}}$$

For Nitric Acid = $HNO_3$ $$H = 1 \cdot -1 = -1$$
$$N = 1 \cdot 0 = 0$$
$$O = 3 \cdot +2 = +6$$
$$\overline{\text{Sum} = +5 \text{ per mole (net oxidizing)}}$$

For Glycine = $NH_2CH_2COOH$ $$C = 2 \cdot -4 = -8$$
$$H = 5 \cdot -1 = -5$$
$$N = 1 \cdot 0 = 0$$
$$O = 2 \cdot +2 = +4$$
$$\overline{\text{Sum} = -9 \text{ per mole (net reducing)}}$$

In the particular instance, it was desired to keep the AMT to glycine molar ratio at 1 to 6. Therefore, the molar ratio of nitric acid to AMT necessary for a stoichiometric burn ratio can be determined as follows.

$$1 \cdot AMT(@-18 \text{ per mole}) = -18 \text{(net reducing)}$$
$$6 \cdot \text{Glycine}(@-9 \text{ per mole}) = -54 \text{(net reducing)}$$
$$\overline{\text{Sum} = -72 \text{(net reducing)}}$$

For a stoichiometric burn ratio, net reducing capacity must be equal to net oxidizing capacity, so the sum of the net oxidizing capacity of the nitric acid needs to be +72.

$$+72 \div +5 \text{ per mole of Nitric Acid} = 14.4 \text{ mole of } HNO_3 \text{ per mole of AMT}$$

In view of the above, the molar ratio of the three reactants required for a stoichiometric burn ratio are as follows.

$$AMT:\text{Glycine}:HNO_3 = 1:6:14.4$$

The amount of water to produce a satisfactory combustion synthesis solution has preferably been found to be ~20 g of D.I. water per 50 g of AMT to be used in the procedure. Generally as little water is used as possible in order to produce a stable solution containing the appropriate amounts of the reagent materials. The recipe for preparing the combustion synthesis solution of the present example is determined as follows:
1) 138.1597 g of AMT (0.045327 mole of AMT)
2) (138.1597 g÷50 g)·20 g $H_2O$=55.26 g of D.I. water needed
3) 14.4·(0.045327 mole)=0.652709 mole of $HNO_3$·63.01 g $HNO_3$ per mole·0.700=58.7531 g of 70% $HNO_3$ solution needed
4) 6·(0.045327 mole)=0.271962 mole of glycine·75.07 g glycine per mole=20.4162 g glycine needed The combustion synthesis solution was prepared in a 500 ml Erlenmeyer flask with a tight fitting screw cap. The AMT was weighed out and transferred to the clean, dry Erlenmeyer flask. D.I. water was then added to the AMT solid in the flask, which was capped and gently shaken periodically until all of the AMT solid had dissolved. The 70% nitric acid solution was slowly added to the flask with periodic shaking. Near the end of the nitric acid addition, a white solid precipitated from the solution. Glycine was then weighed out and also added to the flask. After adding the glycine, the mixture was vigorously shaken to mix the contents. After several minutes the previously precipitated solid had redissolved resulting in a yellow colored solution that was slightly turbid.

The combustion synthesis solution decomposition, or burn, was carried out using a 4 L stainless steel beaker heated on a hotplate to near red heat temperature. After the hotplate has heated the beaker bottom to near red heat, the entire combustion synthesis solution is quickly poured into the hot beaker, then the beaker covered with a clean 100 mesh sieve to contain most of the solid particles produced, while allowing steam and combustion gasses to escape from the beaker. Steam is rapidly evolved for ~5 minutes, then red colored $NO_x$ fumes are evolved as the combustion process begins to initiate. When the $NO_x$ evolution subsides, the beaker containing the porous ash is removed from the hotplate and allowed to cool to room temperature. The entire burn process was completed within less than 10 minutes. After cooling, the dark brown colored ash was recovered from the beaker, and ground to a fine powder (almost gray in color). The finely divided powder was then ready to be reduced to metallic tungsten powder.

Example: 80 at % W-20 at % Nb

In the instant example, an 80 atom % W-20 atom % Nb powder is synthesized that can yield approximately 10 g of a nanocrystalline W—Nb metal powder after reduction. Standard grade AMT was used as the source of tungsten. Ammonium Niobate(V) Oxalate hydrate (ANO; $(NH_4)Nb(O)(C_2O_4)_2 \cdot xH_2O$; F.W.=302.984 g/mole; % Nb by Wt.=20.25%) was used as the source of Nb. Ethanolamine {$(NH_2)CH_2CH_2OH$; F.W.=61.09 g/mole}, 70% nitric acid, and deionized water were also included to form the combustion synthesis solution.

Using the same methodology as described elsewhere herein, the molar ratio of the reactants to produce a stoichiometric burn is as follows.

AMT:ANO:$HNO_3$:Ethanolamine=1:3.00:18.6:4.154

Accordingly, the amounts for preparing the combustion synthesis solution is as follows.
1) 12.2663 g of AMT (0.004024 mole of AMT)
2) ~20 g of D.I. water was used in this procedure
3) 5.5390 g of ANO (0.012073 mole ANO)
4) 18.6·(0.004024 mole)=0.074846 mole of $HNO_3$·63.01 g $HNO_3$ per mole·0.700=6.7372 g of 70% $HNO_3$ solution needed
5) 4.154·(0.004024 mole)=0.016716 mole of ethanolamine·61.09 g ethanolamine per mole=1.0212 g ethanolamine needed The combustion synthesis solution can be prepared in two steps. A first solution containing the above amount of ethanolamine, half of the above amount of the water, and the above amount of the 70% nitric acid solution was prepared then set aside. A second solution containing the above amount of the ANO and half of the above amount of water was first heated gently to dissolve the ANO solid, then the above amount of AMT was added and again gently heated until all of the solids were dissolved. The two solutions were then mixed together to obtain the final combustion synthesis solution.

The combustion synthesis solution is burned in a 600 ml stainless steel beaker, which is heated on a hotplate to near red heat temperature. After the hotplate has heated the beaker bottom to near red heat, the entire combustion synthesis solution is quickly poured into the hot beaker, then the beaker covered with a clean 100 mesh sieve to contain most of the solid particles produced, while allowing steam and combustion gasses to escape from the beaker. Steam is rapidly evolved for ~5 minutes, then red colored $NO_x$ fumes are evolved as the combustion process begins to initiate. When the $NO_x$ evolution subsides, the beaker containing the porous ash is removed from the hotplate and allowed to cool to room temperature. Typically, the entire burn process can be completed within less than 10 minutes. After cooling, the ash is recovered from the beaker, and ground to a fine powder. 12.86 g of the finely divided powder was recovered and was ready to be reduced.

Example: 95 at % W-5 at % Mo

In the instant example, a 95 atom % (97.33 wt %) W-5 atom % (2.67 wt %) Mo powder is synthesized that can yield ~50 g of a nano-particulate W—Mo metal powder. Standard grade AMT was used as the source of W for this procedure. Ammonium Heptamolybdate tetrahydrate (AHM) was used as the source of Mo. Ethanolamine, 70% nitric acid, and deionized water were also included to form the combustion synthesis solution. Using the same methodology as described elsewhere herein, the molar ratio of the reactants required to produce a stoichiometric burn is as follows.

AMT:AHM:$HNO_3$:Ethanolamine=1:0.09:14.724:4.154

The amounts for preparing the combustion synthesis solution was determined as follows:
1) 67.2355 g of AMT (0.022058 mole of AMT)
2) ~100 g of D.I. water was used in this procedure
3) 2.4578 g of AHM (0.001989 mole AHM)
4) 14.724·(0.022058 mole)=0.324782 mole of $HNO_3$·63.01 g $HNO_3$ per mole·0.700=29.2342 g of 70% $HNO_3$ solution needed
5) 4.154·(0.022058 mole)=0.091629 mole of ethanolamine·61.09 g ethanolamine per mole=5.5975 g ethanolamine needed The combustion synthesis solution for this preparation can be done in two steps. A first solution containing the above amount of ethanolamine, half of the above amount of the water, and the above amount of the 70% nitric acid solution was prepared then set aside. A second solution was prepared containing the above amount of the AMT, half of the above amount of water, and the above amount of the AHM. The two solutions were then mixed together to obtain the final combustion synthesis solution.

The combustion synthesis solution burn is carried out using a 4 L stainless steel beaker, which is heated on a hotplate to near red heat temperature. After the hotplate has heated the beaker bottom to near red heat, the entire combustion synthesis solution is quickly poured into the hot beaker, then the beaker covered with a clean 100 mesh sieve to contain most of the solid particles produced, while allowing steam and combustion gasses to escape from the beaker. Steam is rapidly evolved for ~2-3 minutes, then red colored $NO_x$ fumes are evolved as the combustion process begins to initiate. When the $NO_x$ evolution subsides, the beaker containing the porous ash is removed from the hotplate and allowed to cool to room temperature. Typically, the entire burn process can be completed within less than 5 minutes. After cooling, the ash is recovered from the beaker, and ground to a fine powder. 64.78 g of the finely divided powder was recovered and can be reduced.

Example: 96 at % W-4 at % Re (95.95 wt % W-4.05 wt % Re)

In the instant example, a 96 atom % W-4-atom % Re (95.95 wt % W-4.05 wt % Re) powder is synthesized that can yield ~50 g of a nano-particulate W—Re metal powder after reduction. Standard grade AMT was used as the source of W and Ammonium Perrhenate (APR; $NH_4ReO_4$; F.W.=268.24 g/mole; Assay: % Re by Wt.=69.4%) was used as the source of Re for this procedure. Ethanolamine, 70% Nitric Acid Solution, and deionized water were also included to form the combustion synthesis solution.

Using the same methodology as described as described elsewhere herein, the molar ratio of the reactants required to produce a stoichiometric burn is as follows.

$$AMT:APR:HNO_3:Ethanolamine=1:0.5:14.7:4.154$$

The amounts for preparing the combustion synthesis solution are as follows.
1) 66.2825 g of AMT (0.021746 mole of AMT)
2) ~100 g of D.I. water was used in this procedure
3) 2.9300 g of APR (0.010921 mole APR)
4) 14.7·(0.021746 mole)=0.319666 mole of $HNO_3$·63.01 g $HNO_3$ per mole·0.700=28.7730 g of 70% $HNO_3$ solution needed
5) 4.154·(0.021746 mole)=0.090326 mole of ethanolamine·61.09 g ethanolamine per mole=5.5180 g ethanolamine needed The combustion synthesis solution for this preparation can be done in two steps. A first solution containing the above amount of ethanolamine, half of the above amount of the water, and the above amount of the 70% nitric acid solution was prepared then set aside. A second solution containing the above amount of the AMT, half of the above amount of water, and the above amount of the APR was gently heated to dissolve the solids. The two solutions were then mixed together to obtain the final combustion synthesis solution.

The combustion synthesis solution burn is carried out using a 4 L stainless steel beaker, which is heated on a hotplate to near red heat temperature. After the hotplate has heated the beaker bottom to near red heat, the entire combustion synthesis solution is quickly poured into the hot beaker, then the beaker is covered with a clean 100 mesh sieve to contain most of the solid particles produced, while allowing steam and combustion gasses to escape from the beaker. Steam is rapidly evolved for ~7-8 minutes, then red colored $NO_x$ fumes are evolved as the combustion process begins to initiate. When the $NO_x$ evolution subsides, the beaker containing the porous ash is removed from the hotplate and allowed to cool to room temperature. Typically, the entire burn process can be completed within less than 10 minutes. After cooling, the ash is recovered from the beaker, and ground to a fine powder. 64.3278 g of the finely divided powder was recovered and was ready to be reduced.

Example: 90 wt % W-7 wt % Fe-3 wt % Ni

In the instant example, a 90 wt % W-7 wt % Fe-3 wt % Ni powder is synthesized that can yield ~50 g of a nano-particulate W—Fe—Ni metal powder. Standard grade AMT was used as the source of W, Nickel(II) Nitrate hexahydrate $(Ni(NO_3)_2·6H_2O$; F.W.=290.81 g/mole) was used as the source of Ni, and Iron(III) Nitrate nonahydrate $(Fe(NO_3)_3·9H_2O$; F.W.=404.00 g/mole) was used as the source of Fe. Ammonium Citrate (98%) (Am. Citrate; $(NH_4)_3C_6H_5O_7$; F.W.=243.22 g/mole), 70% Nitric Acid Solution, and deionized water were also included in the combustion synthesis solution.

Using the same methodology as described elsewhere herein, the molar ratio of the reactants required to produce a stoichiometric burn is as follows.

$$AMT:Fe(NO_3)_3:Ni(NO_3)_2:HNO_3:Am.\ Citrate=1:3.073:1.252:7.516:3.0$$

The amounts for preparing the combustion synthesis solution are as follows:
1) 62.1719 g of AMT (0.020397 mole of AMT)
2) ~100 g of D.I. water was used in this procedure
3) 25.3256 g (0.062687 mole) of $Fe(NO_3)_3·9H_2O$
4) 7.4294 g (0.025547 mole) of $Ni(NO_3)_2·6H_2O$
5) 3.0·(0.020397 mole)·243.22 g/mole of Ammonium Citrate÷0.98=15.1866 g of Ammonium Citrate
6) 7.516·(0.020397 mole)=0.153304 mole of $HNO_3$·63.01 g $HNO_3$ per mole·0.700=13.8000 g of 70% $HNO_3$ solution needed A 500 ml Erlenmeyer flask with a tight fitting screw cap was used for combustion synthesis solution preparation. The AMT was weighed out and transferred to the clean, dry Erlenmeyer flask. D.I. water was next added to the AMT solid in the flask. Then, the flask was capped and gently shaken periodically until all of the AMT solid had dissolved. The $Fe(NO_3)_3·9H_2O$ was added to the solution in the flask and was dissolved without heat. The $Ni(NO_3)_2·6H_2O$ was then added to the solution in the flask and also dissolved easily without heating. The Ammonium Citrate was dissolved in the solution in the flask. Finally, the 70% nitric acid solution was added to the contents of the flask. Initially, some precipitation occurs that redissolves upon further mixing of the solution. The combustion synthesis solution is then complete.

The combustion synthesis solution burn was carried out using a 4 L stainless steel beaker, which is heated on a hotplate to near red heat temperature. After the hotplate has heated the beaker bottom to near red heat, the entire combustion synthesis solution is quickly poured into the hot beaker, then the beaker was covered with a clean 100 mesh sieve to contain most of the solid particles produced, while allowing steam and combustion gasses to escape from the beaker. Steam is rapidly evolved for ~2-3 minutes, then red colored $NO_x$ fumes are evolved as the combustion process begins to initiate. When the $NO_x$ evolution subsides, the beaker containing the porous ash is removed from the hotplate and allowed to cool to room temperature. The entire burn process is typically completed within less than 10 minutes. After cooling, the ash is recovered from the beaker, and ground to a fine powder. 63.99 g of the finely divided powder was recovered and was ready to be reduced.

Example: Reduction of Combustion Product

As described elsewhere herein, after a combustion synthesis solution has been stoichiometrically burned, the resultant combustion product comprises a metal oxide. The metal oxide powder can then be reduced to yield a nanocrystalline metal powder according to embodiments of the present invention. In the present example, an agglomerate of an as-burnt oxide powder is ground using a mortar and pestle. The oxide powder is then loaded in a metal crucible (tungsten or molybdenum) with a metal cover and placed in a vacuum furnace or a tube furnace. After purging with nitrogen for ~30 min, hydrogen is supplied to the furnace. The oxide powder is reduced under hydrogen at the temperature in the range from 600° to 800° C. up to four hours in order to completely reduce the oxide powder to a nanocrystalline metal powder. To minimize the grain growth of the powder, fast heating and cooling (up to 100° C./min) is preferable. The resultant reduced powder forms moderately hard agglomerates of the metallic nanocrystallites, which can be broken down using a milling technique to achieve better densification.

Figure 2:
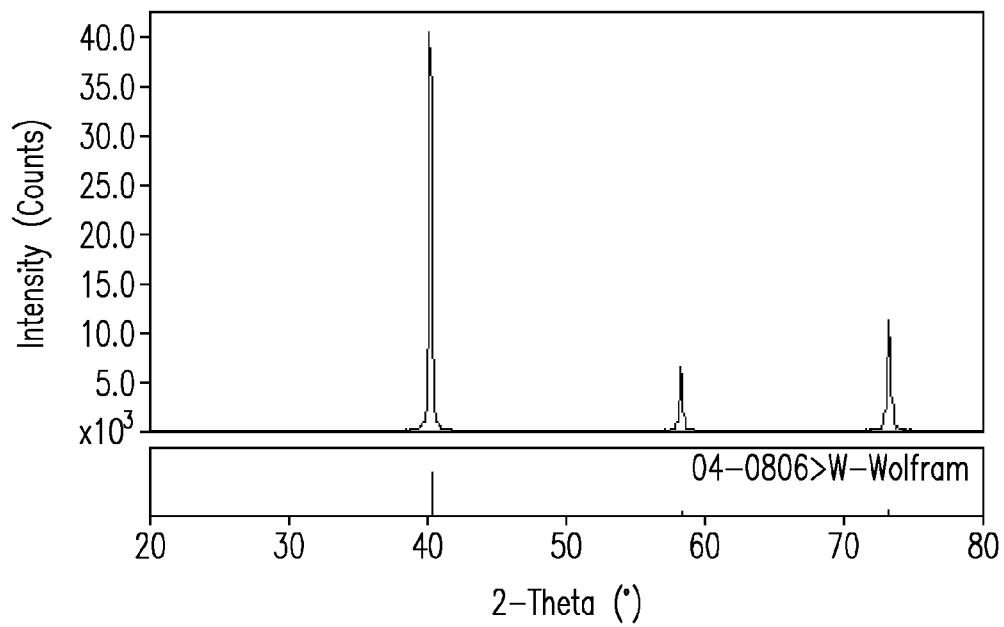
FIG. 2 is an X-ray diffraction pattern of a metallic tungsten powder after reduction of an oxide powder according to embodiments of the present invention.

Referring to FIG. 1, an X-ray diffraction (XRD) pattern is shown for a tungsten oxide powder prior to reduction. The XRD pattern indicates that the major phase is $WO_2$ and that the average grain size is 6.1 nm. Referring to FIG. 2, after reduction at 650° C. for approximately 4 hours, the oxide powder is reduced to metallic tungsten having an average grain size of 45.8 nm.

TABLE 1

Summary of crystallite size for various nanocrystalline metal and/or metal alloy powders synthesized according to embodiments of the present invention.

| Composition | Metal Salt(s) Used | Avg. Alloy Crystallite Size (nm) |
| --- | --- | --- |
| 100W | AMT | 24.1 |
| 99.95W—0.05Ni | AMT, $Ni(NO_3)_2 \cdot 6H_2O$ | 28.3 |
| 99.5W—0.5Ni | AMT, $Ni(NO_3)_2 \cdot 6H_2O$ | 27.2 |
| 97W—3Ni | AMT, $Ni(NO_3)_2 \cdot 6H_2O$ | 28.3 |
| 99W—1$Y_2O_3$ | AMT, $Y(NO_3)_3 \cdot 6H_2O$ | 26.8 |
| 96W—4$Y_2O_3$ | AMT, $Y(NO_3)_3 \cdot 6H_2O$ | 27.6 |
| 95.5W—4$Y_2O_3$—0.5Ni | AMT, $Y(NO_3)_3 \cdot 6H_2O$, $Ni(NO_3)_2 \cdot 6H_2O$ | 30.0 |
| 96W—4Mo | AMT, $(NH_4)_6Mo_7O_{24} \cdot 4H_2O$ | 23.4 |
| 96W—4Re | AMT, $NH_4ReO_4$ | 26.9 |
| 94W—6Nb | AMT, $C_4H_4NNbO_9$ | 23.1 |
| 90W—7Fe—2Ni | AMT, $Fe(NO_3)_3 \cdot 9H_2O$, $Ni(NO_3)_2 \cdot 6H_2O$ | 31.5 |

Referring to Table 1, a summary of crystallite size is provided for a variety of nanocrystalline metal and/or metal alloy powders that were synthesized according to embodiments of the present invention.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. A method for synthesizing powders by a combustion reaction, the method comprising:
   forming a combustion synthesis solution by dissolving in water an oxidizer, a fuel, and at least one base-soluble ammonium metatungstate (AMT) in amounts that yield a stoichiometric burn when combusted;
   heating the combustion synthesis solution to a temperature sufficient to substantially remove the water and to initiate a self-sustaining combustion reaction to form a combustion product of $WO_2$ crystallites of a size less than 60 nm; and
   heating the combustion product for less than 6 hours in a reducing atmosphere at a temperature lower than 850° C. to form the W powder.

2. The method of claim 1, further comprising dissolving a nitrate reagent of an alloying metal in the combustion synthesis solution.

3. The method of claim 2, wherein the oxidizer comprises the nitrate reagent.

4. The method of claim 1, wherein the oxidizer comprises nitric acid.

5. The method of claim 1, wherein the oxidizer comprises ammonium nitrate.

6. The method of claim 1, wherein the fuel comprises glycine.

7. The method of claim 1, further comprising cooling the combustion product to a temperature below 100° C. and then introducing an oxidizing gas to passivate the surface of W powder.

8. A method for synthesizing W nanocrystalline metal powders by a combustion reaction, the method characterized by the steps of:
   forming a combustion synthesis solution by dissolving in water an oxidizer, a fuel, and at least one base-soluble ammonium metatungstate (AMT) in amounts that yield a stoichiometric burn when combusted;
   heating the combustion synthesis solution to a temperature sufficient to substantially remove the water and to initiate a self-sustaining combustion reaction to form a combustion product of $WO_2$ crystallites; and
   heating the combustion product to a temperature below 850° C. in a reducing atmosphere to reduce the $WO_2$ crystallites to W nanocrystalline metal powder.

9. The method of claim 8 wherein the reducing comprises exposing the $WO_2$ crystallites to hydrogen.

10. The method of claim 9 wherein the reducing further comprises heating the $WO_2$ crystallites to a temperature between 600° C. and 800° C.

11. The method of claim 10 wherein the reducing further comprises rapidly heating the $WO_2$ crystallites to the temperature and rapidly cooling the W nanocrystalline metal powder to room temperature.

12. The method of claim 11 wherein the rapid heating and/or cooling is performed at a rate up to 100° C./min.

13. The method of claim 8 wherein the W nanocrystalline metal powder has an average particle size of less than 60 nm.

14. The method of claim 8 wherein the W nanocrystalline metal powder has an average particle size of less than 30 nm.

* * * * *

UNITED STATES PATENT AND TRADEMARK OFFICE
CERTIFICATE OF CORRECTION

PATENT NO.         : 9,802,834 B2                           Page 1 of 1
APPLICATION NO.    : 12/700923
DATED              : October 31, 2017
INVENTOR(S)        : John G. Frye et al.

It is certified that error appears in the above-identified patent and that said Letters Patent is hereby corrected as shown below:

Column 4, Line 1 - Replace "$H_2W_{12}O_{40}.5H_2O$" with --$H_2W_{12}O_{40}\cdot 5H_2O$--

Column 5, Line 53 - Replace "$(O)(C_2O_4)_2.xH_2O$" with --$(O)(C_2O_4)_2\cdot xH_2O$--

Column 8, Line 17 - Replace "$Ni(NO_3)_2.6H_2O$" with --$Ni(NO_3)_2\cdot 6H_2O$--

Column 8, Line 19 - Replace "$Fe(NO_3)_3.9H_2O$" with --$Fe(NO_3)_3\cdot 9H_2O$--

Column 8, Line 34 - Replace "$Fe(NO_3)_3.9H_2O$" with --$Fe(NO_3)_3\cdot 9H_2O$--

Column 8, Line 35 - Replace "$Ni(NO_3)_2.6H_2O$" with --$Ni(NO_3)_2\cdot 6H_2O$--

Column 8, Line 47 - Replace "$Fe(NO_3)_3.9H_2O$" with --$Fe(NO_3)_3\cdot 9H_2O$--

Column 8, Line 48 - Replace "$Ni(NO_3)_2.6H_2O$" with --$Ni(NO_3)_2\cdot 6H_2O$--

Signed and Sealed this
Twenty-sixth Day of June, 2018

Andrei Iancu
*Director of the United States Patent and Trademark Office*